United States Patent [19]
Kraus et al.

[11] Patent Number: 5,895,575
[45] Date of Patent: Apr. 20, 1999

[54] WHOLE BLOOD AND PLATELET LEUKOCYTE FILTRATION APPARATUS

[75] Inventors: Menahem A. Kraus, Rehovot; Yephet Gamlieli, Rishon Lezion; Jacob Yonath, Rehovot; Roni Hazan, Tel Aviv, all of Israel

[73] Assignee: Teva Medical Ltd., Ashdod, Israel

[21] Appl. No.: 08/985,960

[22] Filed: Dec. 5, 1997

Related U.S. Application Data

[60] Continuation of application No. 08/813,213, May 7, 1997, Pat. No. 5,783,094, which is a division of application No. 08/422,274, Apr. 13, 1995, abandoned.

[51] Int. Cl.$^6$ .................... B01D 39/00; B01D 71/10
[52] U.S. Cl. .............. 210/483; 210/488; 210/490; 210/496; 210/500.24; 210/500.29; 210/503; 210/504; 210/506; 210/508
[58] Field of Search .................... 210/483, 488, 210/490, 496, 500.24, 503, 504, 505, 506, 507, 508, 500.29; 427/244, 245, 246; 428/304.4, 403, 474.4, 480; 422/55, 56

[56] References Cited

U.S. PATENT DOCUMENTS

| | | | |
|---|---|---|---|
| 4,416,777 | 11/1983 | Kuroda et al. | 210/446 |
| 4,964,989 | 10/1990 | Gsell | 210/490 |
| 5,023,052 | 6/1991 | Nagatomo et al. | 422/56 |
| 5,053,133 | 10/1991 | Klein et al. | 210/500.38 |
| 5,091,086 | 2/1992 | Stengaard | 210/490 |
| 5,478,470 | 12/1995 | Fukuda et al. | 210/505 |
| 5,496,708 | 3/1996 | Kawasaki et al. | 422/56 |
| 5,707,526 | 1/1998 | Kraus et al. | 210/483 |

*Primary Examiner*—John Kim
*Attorney, Agent, or Firm*—Mark M. Friedman

[57] ABSTRACT

A method for selectively removing leukocytes from a suspension which also contains platelets, such as a platelet concentrate or whole blood. The method includes passing the suspension through a filter which includes a polysaccharide-type coating. The coating may include one or more of hydroxypropylmethyl cellulose, hydroxybutylmethyl cellulose, dextran and hydroxyethyl starch. Also provided is a filter for selectively removing leukocytes from a suspension which also contains platelets. The filter includes a substrate which is coated with a polysaccharide-type composition.

7 Claims, No Drawings

WHOLE BLOOD AND PLATELET LEUKOCYTE FILTRATION APPARATUS

This Application is a Continuation of U.S. application Ser. No. 08/813,213, filed on Mar. 7, 1997, U.S. Pat. No. 5,783,094, which is a Divisional of U.S. application Ser. No. 08/422,274, filed on Apr. 13, 1995, abandoned.

FIELD AND BACKGROUND OF THE INVENTION

The present invention relates to methods of removing leukocytes from whole blood or platelet concentrates.

It is widely known that for the vast majority of transfusion therapies it is desirable to remove the leukocytes from donated blood, typically by filtration, prior to the transfusion of the various blood components into a patient.

It is desirable to remove the leukocytes since their presence may have adverse effects on the patient. For example, leukocytes may cause non-hemolytic febrile reactions and/or HLA allo-immunization. Leukocytes may also induce graft versus host reactions. In addition, leukocytes present in contaminated blood may harbor various viruses. At the same time, the removal of the leukocytes does not generally have negative implications for the recipient since the leukocytes serve no useful purpose in the vast majority of transfusions.

The current practice is to remove the leukocytes from the various blood components after these have been separated from whole blood. Thus, each portion of whole blood is typically first separated, e.g., by centrifuging and/or filtration, into a number of components or fractions, principally (1) packed erythrocytes (red blood cells); (2) platelet concentrate; and (3) plasma. Each of the fractions then undergoes separate treatment, typically filtration, to remove the leukocytes present in that fraction.

For example, in PCT/US94/01413 the present inventors describe unique, membrane-based filters for removing leukocytes from packed red blood cells or for removing both leukocytes and platelets from whole blood. The filters described in PCT/US94/01413 capture platelets and are thus unsuitable for the removal of leukocytes from platelet concentrates or from whole blood.

A difficulty with filters such as those disclosed in PCT/US94/01413 is that they are limited to treatment of specific blood fractions rather than to whole blood. This limitation makes it necessary to carry out a number of separate filtrations, each using a specific filter, to separately remove the leukocytes from each of the blood fractions.

It would be advantageous to have an efficient filter capable of selectively removing leukocytes from whole blood, i.e., a filter which would effectively capture leukocytes while effectively passing the other blood components, including the plasma, red blood cells and the platelets.

The ability of selectively removing leukocytes from whole blood with the attendant recovery of red cells and platelets would have significant operational and cost advantages. In practice, whole blood would then be filtered to remove leukocytes only once, preferably in the blood bank. Following this filtration, the leukocyte-free blood would be separated, as by centrifugation, into leukocyte-free fractions and processed in the usual manner.

The removal of leukocytes from whole blood requires a special filter which captures leukocytes but passes red blood cells and platelets. Currently, no such filter is commercially available, although at least one such filter is described in the literature. Specifically, a whole blood leukocyte filter is disclosed in U.S. Pat. No. 4,985,153. However the performance of that filter, as described in the above-referenced patent, is far from satisfactory, considering current internationally accepted standards. Current international standards call for residual leukocytes of no more than $5 \times 10^6$ per unit of blood. Platelet recovery is expected to be no less than 70%.

There is thus a need for, and it would highly advantageous to have, a universal filter exhibiting high platelet recovery and very high leukocyte retention.

SUMMARY OF THE INVENTION

According to the present invention there is provided a method for selectively removing leukocytes from a suspension which also contains platelets, comprising passing the suspension through a filter which includes a polysaccharide-type coating.

Also according to the present invention there is provided a filter for selectively removing leukocytes from a suspension which also contains platelets, comprising: (a) a substrate; and (b) a coating on the substrate which includes a polysaccharide-type composition.

Finally according to the present invention there is provided a process for preparing a filter for selectively removing leukocytes from a suspension which also contains platelets, comprising the steps of: (a) providing a coating solution including a polysaccharide-type composition and a solvent; (b) applying the coating solution to a substrate; and (c) drying the coated substrate to form a dry coated substrate.

According to further features in preferred embodiments of the invention described below, the polysaccharide-type composition includes one or more of hydroxypropyl cellulose, hydroxyethyl cellulose, hydroxypropylmethyl cellulose, hydroxybutylmethyl cellulose, dextran and hydroxyethyl starch.

The present invention successfully addresses the shortcomings of the presently known configurations by providing a method and apparatus for efficiently selectively removing leukocytes from suspensions, such as blood and blood fractions, which also contain platelets.

The method and apparatus involves use of a membrane and/or non-woven material coated with a polysaccharide-type composition through which a suspension containing both leukocytes and platelets is passed. It has been found that this method and apparatus are effective in passing the platelets while retaining the leukocytes.

DESCRIPTION OF THE PREFERRED EMBODIMENTS

The present invention is of a method and apparatus for efficiently selectively removing leukocytes from whole blood or from a blood fraction which contains platelets.

The principles and operation of the present invention will be better understood with reference to the following description and examples.

It is known in the literature that filtration can be used to recover platelets from leukocyte-free blood through the use of very specific surface treatments of the filter medium. In the absence of these treatments the filter will retain a large proportion of the platelets.

Two types of such surface treatments are described in the literature. U.S. Pat. No. 4,936,998 discloses the surface coating of preformed acrylic copolymers, such as copoly (hydroxyethyl methacrylate-diethylaminoethyl methacrylate). U.S. Pat. No. 4,880,548 discloses the grafting of certain monomers, such as acrylate, onto the surface. It is noted parenthetically that U.S. Pat. No. 4,880,548 asserts that in order to obtain efficient platelet filtration a filter is required which features critical wetting surface tension of 90 dyn/cm or more.

None of the commercially available platelet concentrate leukodepletion filters is suitable for recovery of platelets from whole blood since the presence of red blood cells along with platelets serves to rapidly clog these filters.

It has been unexpectedly found that coating of a suitable filter media using simple commercially available polysaccharides and polysaccharide derivatives (referred to herein singly and collectively as a "polysaccharide-type composition") makes it possible to construct highly efficient platelet filters which operate to remove leukocytes from platelet concentrates. Similar treatments can be used to make a highly efficient universal filter which efficiently removes leukocytes from whole blood. Thus, methods and filters according to the present invention are suitable for the removal of leukocytes, with minor modifications, for both platelet and whole blood filtration.

Various polysaccharide-type compositions are suitable in a method and filter according to the present invention. Examples include various cellulose derivatives, including but not limited to, hydroxypropyl cellulose (HPC), hydroxyethyl cellulose (HEC), hyrdroxybutylmethyl cellulose, hyrdroxypropylmethyl, cellulose dextran and hydroxyethyl starch. Preferred polysaccharide-type compositions include hydroxypropyl cellulose, hydroxypropylmethyl cellulose and hydroxybutylmethyl cellulose. The most preferred polysaccharide-type composition is hydroxypropyl cellulose. The various polysaccharide-type compositions are generally soluble in water and a number of other solvents, such as ethanol.

A dilute solution, typically in water, of one or more of these polymers is used as a coating solution to coat the surface of the filter substrate or medium. A preferred solution is an aqueous HPC solution with an HPC concentration of from about 0.1 to about 10% wt/vol. Most preferred is a concentration of from about 0.5 to about 3% wt/vol.

The filter substrate may be any suitable medium, preferably one or more non-woven sheets or one or more membranes. Most preferably, the filter substrate includes both one or more non-woven sheets and one or more membranes. As used herein, the term 'membrane' is intended to include a continuous, nonfibrous porous matrix.

Membranes for use in the present invention may be made of any suitable material, including but not limited to, polycarbonate, acrylic copolymer, polyvinyl chloride, nylon and nitrocellulose. Preferably, the membrane features a pore size of from about 2 to about 20 µ.

Non-woven materials for use in the present invention may be made of any suitable material, including but not limited to, polyester, cellulose, nylon and polypropylene.

To produce a properly coated filter medium, typically membrane and/or non-woven, a coating solution, typically in water or ethanol, which includes a polysaccharide composition is provided. The filter substrate is then coated, as by dipping, with the coating solution. The filter is then dried at any suitable temperature, such as near room temperature or at elevated temperatures to evaporate the solvent and form a dry coated substrate.

To provide for better bonding between the polysaccharide-type composition and the substrate it may be desirable to provide a cross-linking agent in the coating solution. Any suitable cross-linking agent may be used, including but not limited to a melamine, such as hexamethoxymethyl melamine, a polyepoxide, or a polyaldehyde. Upon drying the cross-linking agent reacts with the polysaccharide-type composition and renders it insoluble. Depending on the substrate chemistry, the cross-linking agent may also react with the substrate serving to bind the polysaccharide-type composition tightly to the substrate so as to preclude the possibility of the separation of the coating from the substrate.

Optionally, regardless of whether curing is used, it may be desirable to wash the dry coated substrate with a suitable washing medium, such as water or ethanol, and subsequently re-dry the washed coated substrate. Even in the absence of cross-linking, sufficient coating material may remain on the substrate to be effective.

The coating of the filter substrate as described above has been found to have a dramatic beneficial effect on platelet passage through the filter despite the fact that the coated substrate has a surface tension of only about 70 dyn/cm.

Whereas many untreated filter media, such as polyester, nylon, nitrocellulose, with pore size of 2–20 µm retain all or a very significant fraction of the platelets, following treatment with a polysaccharide-type composition, platelet recovery is typically from about 80 to about 100%. While at times the retention of white cells is also slightly reduced by the treatment, the effect is not nearly as pronounced as the increase in platelet recovery. In this way, a good separation between leukocytes and platelets can be achieved.

Because of their flexible membrane and poor adhesion, red cells pass easily through filters of the present invention. Thus, a universal filter, which is able to selectively remove leukocytes from all other blood components is achieved.

As demonstrated in the examples below, with the appropriate number and porosity of layers of filter media, highly efficient leukocyte-removing filters for platelet concentrates and for whole blood can be constructed.

The most preferred filter configuration includes two layers: (1) a non-woven filter layer and a membrane filter layer. Each of the layers may include multiple filter sheets. Both layers are treated with the polysaccharide-type composition as described above. A typical filter, made as described, yields platelets recovery of greater than 70% and leukocyte retention of greater than 99% in both platelet concentrate filtration and whole blood filtration.

EXAMPLES

Examples 1–23 relate to the filtration of platelet concentrates while Examples 24–28 relate to the filtration of whole blood.

Examples 1–6

Effect of Coating on Membrane Performance

Various membranes were treated by dipping into a solution of 1% hydroxypropyl cellulose (HPC) in water. The membranes were then allowed to dry at ambient conditions. The treated membranes and untreated controls were tested for passage of platelets and white blood cells from standard platelet concentrates. The results are summarized in Table 1. As can be clearly seen, the treatment dramatically improves platelet passage and flow rate.

TABLE 1

Filtration of Platelet Concentrates (PC) Through Coated Membrane Filters

| Example | Membrane | Pore size (μm) | Treatment | No. of Layers | Flow Rate ml/min | Cell Passage PLT % | Cell Passage WBC % |
|---|---|---|---|---|---|---|---|
| 1 | Polycarbonate (PC,-Poretics) | 2 | Untreated | 1 | 0 | 0 | 0 |
|   |   |   | Coated | 1 | 0.3 | 100 | 30 |
| 2 | Acrylic copolymer (Versapore, Gelman) | 3 | Untreated | 1 | 0 | 1 | 0 |
|   |   |   | Coated | 1 | 0.5 | 75 | 17 |
| 3 | PVC (GLA-5000, Gelman) | 5 | Untreated | 1 | 0 | 0 | 0 |
|   |   |   | Coated | 1 | 0.3 | 32 | 0 |
| 4 | Nylon (Magna-Nylon, MSI) | 10 | Untreated | 1 | 0.1 | 13 | 0 |
|   |   |   | Coated | 1 | 0.8 | 75 | 14 |
| 5 | Nylon (Magna-Nylon, MSI) | 20 | Untreated | 1 | 0.9 | 77 | 32 |
|   |   |   | Coated | 2 | 3.8 | 96 | 11 |
| 6 | Nitrocellulose (NC, AE100, S&S) | 12 | Untreated | 2 | 0.7 | 32 | 18 |
|   |   |   | Coated | 2 | 9.0 | 92 | 13 |

Examples 7–10

Effect of Coating on Non-Woven Filter Performance

Various Polyester non-woven filters were treated by dipping the filter substrate in 1% aqueous or ethanol HPC solution and drying.

Multilayer arrays of treated filters and untreated controls were used to filter platelet concentrates. The results are summarized in Table 2.

It is clearly seen that the passage of platelets is very substantially improved following treatment, while the passage of white cells increases to a much smaller extent.

TABLE 2

Filtration of Platelets Concentrates Through Coated Non-wovens

| Example | Filter | Treatment | No. of Layers | Flow Rate ml/min | Cell Passage PLT % | Cell Passage WBC % |
|---|---|---|---|---|---|---|
| 7 | Polyester 80 g/m², Sodoca | Untreated | 10 | 86 | 55 | 15 |
|   |   | Coated | 10 | 40 | 100 | 35 |
|   |   | Coated | 30 | 6 | 94 | 5 |
| 8 | Polyester 100 g/m², Sodoca | Untreated | 10 | 7 | 24 | 9 |
|   |   | Coated | 10 | 3 | 100 | 29 |
| 9 | Polyester 120 g/m², Freudenberg | Untreated | 10 | 3* | 19 | 0 |
|   |   | Coated | 10 | 3* | 86 | 9 |
| 10 | Cellulose 11 μ (Whatman) | Untreated | 6 | 0.7 | 83 | 20 |
|   |   | Coated | 6 | 2 | 96 | 40 |

*Flow adjusted to 3 ml/min.

Examples 11–15

Effect of the Concentration of the Coating Solution

The coating effect is concentration dependent as shown in Table 3. The model filters used were a combination of membranes and non-woven sheets. As shown, HPC concentration of 0.5% (wt/vol) and higher ensures good flow, good platelet passage and little white cell leakage.

TABLE 3

Effect of HPC Coating Concentration on Filter Performance

Filter Composition: Polyester 120 g/m² Sheets (6 layers)
Nitrocellulose membrane: AE100 (3 layers)
Filter treatment: HPC coating
Flow Rate: Adjusted to 1.0–1.5 ml/min

| Example | HPC Concen. (%) | Vol. (ml) Filtered Before Clogging | Cell Passage PLT % | Cell Passage WBC % |
|---|---|---|---|---|
| 11 | 0 | <6 | 9 | 2 |
| 12 | 0.25 | <23 | 79 | 4 |
| 13 | 0.5 | >30 | 84 | 5 |
| 14 | 1.0 | >30 | 85 | 3 |
| 15 | 2.0 | >30 | 89 | 5 |

Examples 16–18

Effect of Coating Cross Linking

The filter coating was cross-linked for improved stability. The cross-linking agent used was hexamethoxymethyl melamine. Table 4 summaries results from a number of treatment variables.

It is shown that cross-linking, alone or in conjunction with subsequent washing, apparently has little effect on either platelet or white cell passage. However, the amount of extractable material lost upon washing is substantially reduced.

TABLE 4

Cell Separation Following Various Filter Treatments

Filter composition: Polyester 120 g/m² sheet (8 layers) and AE (3 layers)

| Example | Filter and Treatment | Cell Passage PLT % | Cell Passage WBC % |
|---|---|---|---|
| 16 | 2% HPC | 89 | 3 |
| 17 | 2% HPC + Cross Linking | 87 | 2 |
| 18 | 2% HPC + Cross Linking + Washing | 88 | 2 |

Examples 19–23

Full Scale Platelet Filters

Full scale platelet filters, suitable for 4 to 5 pooled units, were constructed from a layered structure of surface treated non-woven materials and treated membranes. Construction and performance data are summarized in Table 5.

TABLE 5

Performance of Full Scale Platelet Filters

| Ex. | Filter Composition | No. of Layers | Vol. Filtered (ml) | Platelet Recovery (%) | WBC Removal (%) | Residual WBC per µl | Residual WBC Total |
|---|---|---|---|---|---|---|---|
| 19 | Polyester 80 g/m² AE-100 (12 µ) | 32 3 | 200 | 98 | 99.95 | 0.25 | $0.1 \times 10^6$ |
| 20 | Polyester 100 g/m² AE-100 (12 µ) | 20 4 | 250 | 94 | 99.83 | 1.1 | $0.25 \times 10^6$ |
| 21 | Polyester 100 g/m² AE-100 (12 µ) | 16 5 | 200 | 95 | 99.74 | 1.4 | $0.27 \times 10^6$ |
| 22 | Polyester 100 g/m² AE-100 (12 µ) | 20 5 | 200 | 100 | 99.70 | 1.6 | $0.32 \times 10^6$ |
| 23 | Polyester 100 g/m² AE-100 (12 µ) | 20 5 | 230 | 88 | 99.81 | 1.1 | $0.25 \times 10^6$ |

Treatment:
a. Filters 19 and 21—coating (1% HPC)
b. Filters 20 and 22—coating and cross-linking (0.025% melamine)
c. Filter 23—coating, cross-linking and washing

Example 24
Hydroxypropyl Cellulose Coating (Whole Blood)

A 0.1% aqueous solution of hydroxypropyl cellulose (HPC) of 370000 MW was used. The filter materials included nitrocellulose membranes of nominal pore size 12 and 8 microns, and a 120g/m² non-woven polyester fabric.

The filter materials were dipped in the HPC solution for 5 minutes at room temperature. The non-woven fabric was squeezed to remove excess solution. The membranes were treated similarly, but were not squeezed. After 24 hours of drying at room temperature a filter was constructed in a plastic holder of 43 cm² filtration area. The filter was made up of two layers of 8 µ membrane, two layers of 12 µ membrane and 20 layers of non-woven fabric serving as a pre-filter. Another four layers of the same non-woven fabric were introduced between adjacent membranes to serve as separators. Four hundred seventy ml of whole blood were collected into a standard collection bag using CPD anticoagulation solution and filtered 6 hours after donation. Filtration time was 27 minutes at a pressure head of 0.09 atm. Leukocyte content was reduced from 6300/µl in the original blood to 4/µl in the filtered blood. Seventy two percent of the original platelets (185000/µ) were recovered. The erythrocyte content of the filtered blood was reduced by only 0.5%. When the same experiment was repeated without applying HPC coating to the filter layers only 1–5% of the platelets were recovered.

Example 25
Effect of Washing, (Whole Blood)

The procedure of Example 24 was repeated except that the 8 µ membrane was omitted, and a 1% solution of HPC was used. In addition, after the dip-coated membranes and pre-filters were dried, they were washed by soaking in water at 22° C. for 20 min. Twenty hours old whole blood was filtered in this system at a rate of 485 ml/11 min. Leukocyte reduction was from 5000/µl to 15/µl. Platelet recovery was 216000/µl out of 282000/µl in the original blood.

Repeating this experiment without applying the HPC coating resulted in only a 1–5% platelet recovery.

Example 26
Hydroxypropyl-methyl Cellulose Coating (Whole Blood)

The same filter structure as in Example 24 was used for filtration of 6 hours old whole blood. Coating was performed using a 0.6% aqueous solution of hydroxypropyl-methyl cellulose (M.W. 86000; hydroxypropyl content: 10%, methyl content: 30%) containing 0.016% glyoxal as cross-linking agent. After dipping, membranes and pre-filters were baked at 108–115° C. for 40 minutes, washed and dried as per Example 25.

Filtration rate was 470ml/33min. Leukocytes were reduced from 5600/µl to 7/µl and platelet recovery was 182000/µl out of 21 6000/µl in the original blood.

Example 27
Hydroxybutyl-methyl Cellulose Coating (Whole Blood)

The procedure of Example 26 was repeated except that four 12 µ membranes were used and a 0.5% hydroxybutyl-methyl cellulose solution in a 9:1 water ethanol mixture was used as coating solution. No cross-linking agent was used, and the baking and washing steps were omitted. Four hundred forty ml of whole blood were filtered in 25 minutes. Platelet recovery was 73%, and leukocyte content was reduced from 7800/µl to 300/µl.

Example 28
Hydroxyethyl Cellulose Coating (Whole Blood)

The procedure of Example 26 was repeated using four 12 µ membranes and a coating solution made up of a 1% hydroxyethyl cellulose aqueous solution containing 0.04% glyoxal as cross-linking agent. 530 ml of 6 hours old whole blood were filtered in 19 minutes. The leukocyte count was reduced from 6200/µl to 300/µl and platelet recovery was 45%.

While the invention has been described with respect to a limited number of embodiments, it will be appreciated that many variations, modifications and other applications of the invention may be made.

What is claimed is:

1. A filtering device with multiple layers for selectively removing leukocytes from a suspension which also contains platelets, wherein leukocytes are captured by the multiple layers, while the platelets pass through the device, the device comprising at least two layers of nitrocellulose membranes having a pore size of from about 5 to about 15 microns, and at least two layers of non-woven fibrous porous sheets, both said nitrocellulose membranes and said non-woven fibrous porous sheets being coated with at least one polysaccharide-type material.

2. The filtering device of claim 1 wherein said polysaccharide-type materials are selected from the group consisting of hydroxypropyl cellulose, hydroxyethyl cellulose, hydroxypropylmethyl cellulose, hydroxybutylmethyl cellulose, dextran and hydroxyethyl starch.

3. The filtering device of claim 1, wherein said non-woven fibrous porous sheet is a polyester.

4. The filtering device of claim 1, wherein said polysaccharide-type materials are selected from the group consisting of hydroxypropyl cellulose, hydroxypropylmethyl cellulose and hydroxybutylmethyl cellulose.

5. The filtering device of claim 1, wherein the polysaccharide-type material is hydroxypropyl cellulose.

6. A filtering device with multiple layers for selectively removing leukocytes from a suspension which also contains platelets, wherein leukocytes are captured by the multiple layers, while the platelets pass through the device, the device comprising at least three nitrocellulose membranes having a pore size of from about 5 to about 15 microns, and at least three layers of non-woven fibrous porous sheets, both said nitrocellulose membranes and said fibrous sheets being coated with at least one polysaccharide-type material.

7. The filtering device of claim 6, comprising at least eight nitrocellulose membrane layers and at least sixteen non-woven fibrous porous sheet layers.

* * * * *